US006336931B1

(12) United States Patent
Hsu et al.

(10) Patent No.: US 6,336,931 B1
(45) Date of Patent: Jan. 8, 2002

(54) AUTOMATIC BONE DRILLING APPARATUS FOR SURGERY OPERATION

(75) Inventors: Yeh-Liang Hsu, No. 5, Aly.2, Ln.299, Kuo-Chiang 2 St., TaoYuan City, TaoYuan Hsien; Shih-Tseng Lee, 10F, No.3, Ln.334, Sec.2, Chien-Kuo S. Rd.; Chong-Fai Wang, both of Taipei; Jia-Wen Chen, ChangHua; Hao-Wei Lin, Hsinchu; Tsung-Cheng Huang, MiaoLi, all of (TW)

(73) Assignees: Yeh-Liang Hsu, TaoYuan; Shih-Tseng Lee, Taipei, both of (TW)

( * ) Notice: Subject to any disclaimer, the term of this patent is extended or adjusted under 35 U.S.C. 154(b) by 0 days.

(21) Appl. No.: 09/572,445

(22) Filed: May 17, 2000

(51) Int. Cl.$^7$ ................................................ A61B 17/16
(52) U.S. Cl. ........................................ 606/80; 606/130
(58) Field of Search ................................ 606/1, 79, 80, 606/96, 130, 180; 408/3

(56) References Cited

U.S. PATENT DOCUMENTS

| | | | |
|---|---|---|---|
| 3,576,540 A | * | 4/1971 | Fair ........................ 340/172.5 |
| 4,043,700 A | * | 8/1977 | Singer ......................... 408/237 |
| 5,154,717 A | * | 10/1992 | Matsen, III et al. .......... 606/53 |
| 5,598,512 A | * | 1/1997 | Niwa .......................... 395/61 |
| 5,914,882 A | * | 6/1999 | Yeghiazarians ........ 364/474.19 |

* cited by examiner

Primary Examiner—Eduardo C. Robert
(74) Attorney, Agent, or Firm—Troxell Law Office PLLC

(57) ABSTRACT

An automatic bone drilling apparatus for surgery operation uses a computer to control a hand tool drilling device to drill opening in skeleton. The computer has a fuzzy logic software to control the hand tool operation through a control box and a manual-automatic mode switch box. The hand tool drilling device may be securely mounted on the patient. Drilling location and size and depth may be precisely controlled to enhance surgical operation safety. It is particularly useful for drilling patient skeleton for brain surgery operation.

16 Claims, 4 Drawing Sheets

AUTOMATIC BONE DRILLING APPARATUS FOR SURGERY OPERATION

FIELD OF THE INVENTION

This invention relates to a bone drilling apparatus for surgery operation that uses a computer to receive data signals from a manual drilling hand tool and perform a fuzzy control process for enhancing safety of the surgical operation.

BACKGROUND OF THE INVENTION

Nowadays with continuous enhancing of living standard in most countries, there is an increasing demand for high quality health care. In surgery operation, as the stake and risks is particularly high, a great deal of medical instruments have been developed to enhance the operation precision and safety. This is particularly true for brain surgery. As brain is a very critical organ of human body and is very delicate, the precision and reliability of medical facilities and instruments for brain surgery operation is very important. Conventional brain surgery operation usually should be preceded by computerized tomography of head for determining disease exact location. Then a drilling hand tool will be used to drill through the skeleton of the patient to make an opening for surgical operation use. The skeleton is covered by skin and hairs from outside. Inside the skeleton, there are different layers of brain membranes such as Dura mater, Pia mater and Arachnoid and a lot of vessels embedded therein. The drilling of the skeleton demands a great precision. A slightest wrong doing could cause brain damage and result in several consequence. Even aiding by medical instruments, contemporary brain surgery operation is still highly relied on surgeon's skills and experiences. There is a great demand for a high precision medical facility that can automatically drill skeleton of the patient at an exact spot to an exact depth and size to alleviate the burden of the surgeon so that they may have more energy and concentration to perform more delicate and demanding brain surgical operation.

SUMMARY OF THE INVENTION

It is therefore an object of this invention to provide an automatic bone drilling apparatus that uses a computer to control a drill operation through a software made by fuzzy principle so that skeleton drilling operation may be done with great precision and at an enhanced safety level.

In one aspect, the skeleton drilling apparatus of this invention includes an automatic feeding means to facilitate steady operation and a strut for securely holding an electric drill. There is a control box to receive signals from the drill and to feed the signals to the computer. The computer is run by a fuzzy logic software and feedback to the control box for actuating the drill to perform bone drilling desired.

In another aspect, an oscilloscope is provided and connected with the control box for indicating drilling status to the surgeon.

In a further aspect, a manual/automatic mode switch box is provided to connect with the control box so that skeleton drilling may be done either manually or automatically at surgeon's selection. The actual drilling is done by surgeon through an electrical drill driven by a motor. It may be flexibly deployed and used based on requirements and different situations.

BRIEF DESCRIPTION OF THE DRAWINGS

The invention, as well as its many advantages, may be further understood by the following detailed description and drawings in which.

DETAILED DESCRIPTION OF THE PREFERRED EMBODIMENT

This invention aims at providing an automatic bone drilling apparatus for surgery operation, particularly brain surgery operation. It is an auxiliary facility for enhancing surgery operation safety and process, and reducing the risk of injuring patient's brain. This invention includes a drilling hand tool controlled by a computer and a control unit. It may be used by experienced surgeons for precisely locating bone drilling position and making a bone opening required safely and smoothly to facilitate the delicate brain surgical operation needed.

Figure 1:
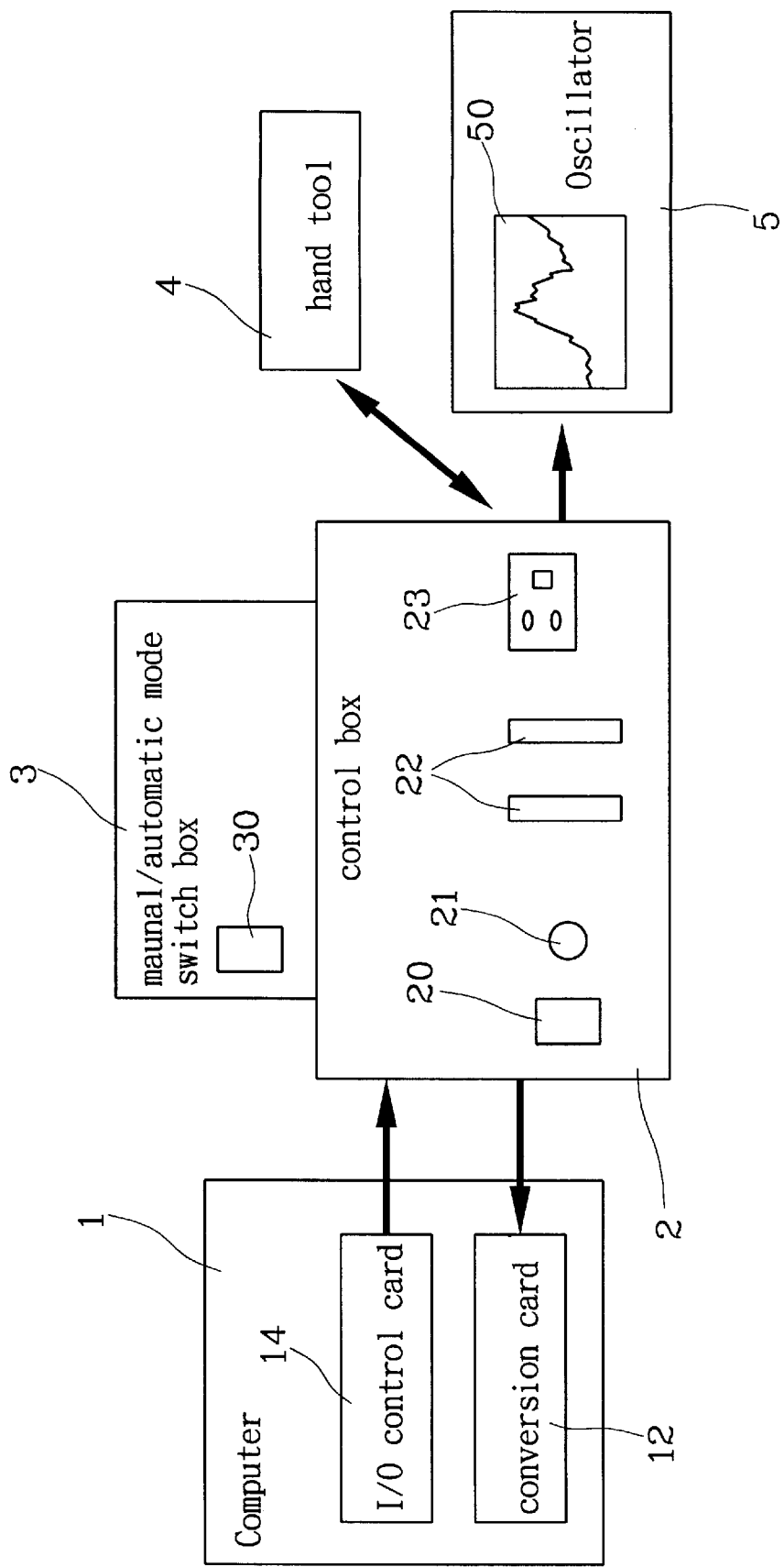
FIG. 1 is a schematic diagram showing components relationship of this invention.

Referring to FIG. 1, this invention includes a computer 1 linking with a control box 2 for controlling a hand tool 4 which may be used for drilling. The control box 2 also wires with a manual/automatic mode switch box 3 for selecting drilling operation mode desired. The control box 2 may further connect with an oscilloscope 5 which has a display screen 50 for displaying current signal at the handle tool 4 which links to the control box 2. In the computer 1, there is an input/output control card 14 for generating control signal to the control box 2 and an A/D conversion card 12 for receiving signals from the control box 2 and converting the signals for computer process. The control box 2 is activated by electric voltage and includes a power switch 20 for power turn-on or turn-off of the control box 2, an indicator light 21 for alerting if a through opening has been attained in the skeleton drilling operation, a plurality of connector slots 22 for coupling with connection interface cards to transmit signals with the computer 1 to the manual/automatic mode switch box 3, hand tool 4 oscillator 5, and a hand tool output 23 for supplying power for the hand tool 4. The signal of drilling statues also is transmitted to the control box 2 through the hand tool output 23.

In this invention, the computer has a software which is designed by fuzzy logic to perform process and sending control signals to the control box 2 which in turn controls drilling operation of the hand tool 4. Details of fuzzy logic principle used in the software will be elaborated later.

Figure 2:
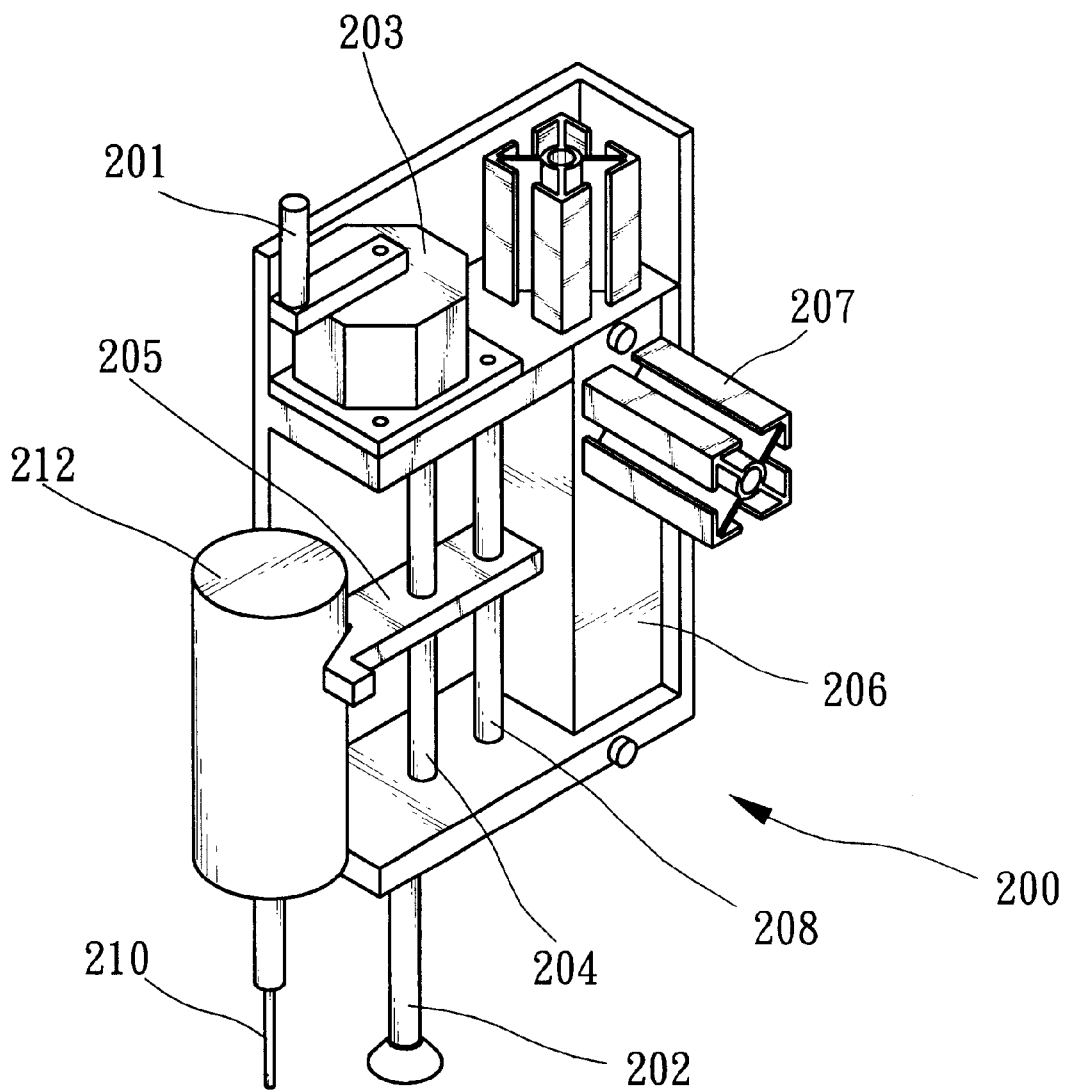
FIG. 2 is a perspective view of a drilling hand tool of this invention.

FIG. 2 shows the structure of the hand tool which includes a drilling device 200. It has a drill gimlet 210 for making an opening in the skeleton. The drilling gimlet 210 is driven by a DC motor 212 which is held by a slide block 205. The slide block 205 may be moved up or down by a step motor 203 along a tooth rack 204 so that the drill gimlet 210 will also be moved up or down during drilling operation. The slide block 205 further engages with a guiding bar 208 for holding the slide block 205 to move up and down steadily without swinging angularly. The drilling device 200 also has a rotation handle bar 201 which may be used to control the step motor 203 for manual drilling operation. The automatic or manual drilling selection is done by means of the manual/automatic mode switch box 3 through the control box 2.

There is also a strut 202 located below the drilling device for supporting the drilling device securely and steadily during drilling operation. Inside the drilling device, there is a pillar 206 which has a holding bar 207 extending transversely outward for people to hold the whole drilling device 200 steadily. By means of the strut 202 and the holding bar 207, the drilling device 200 may be held securely and steadily to enable surgeons to perform highly delicate and precious skeleton or skeleton drilling operation.

Figure 3:
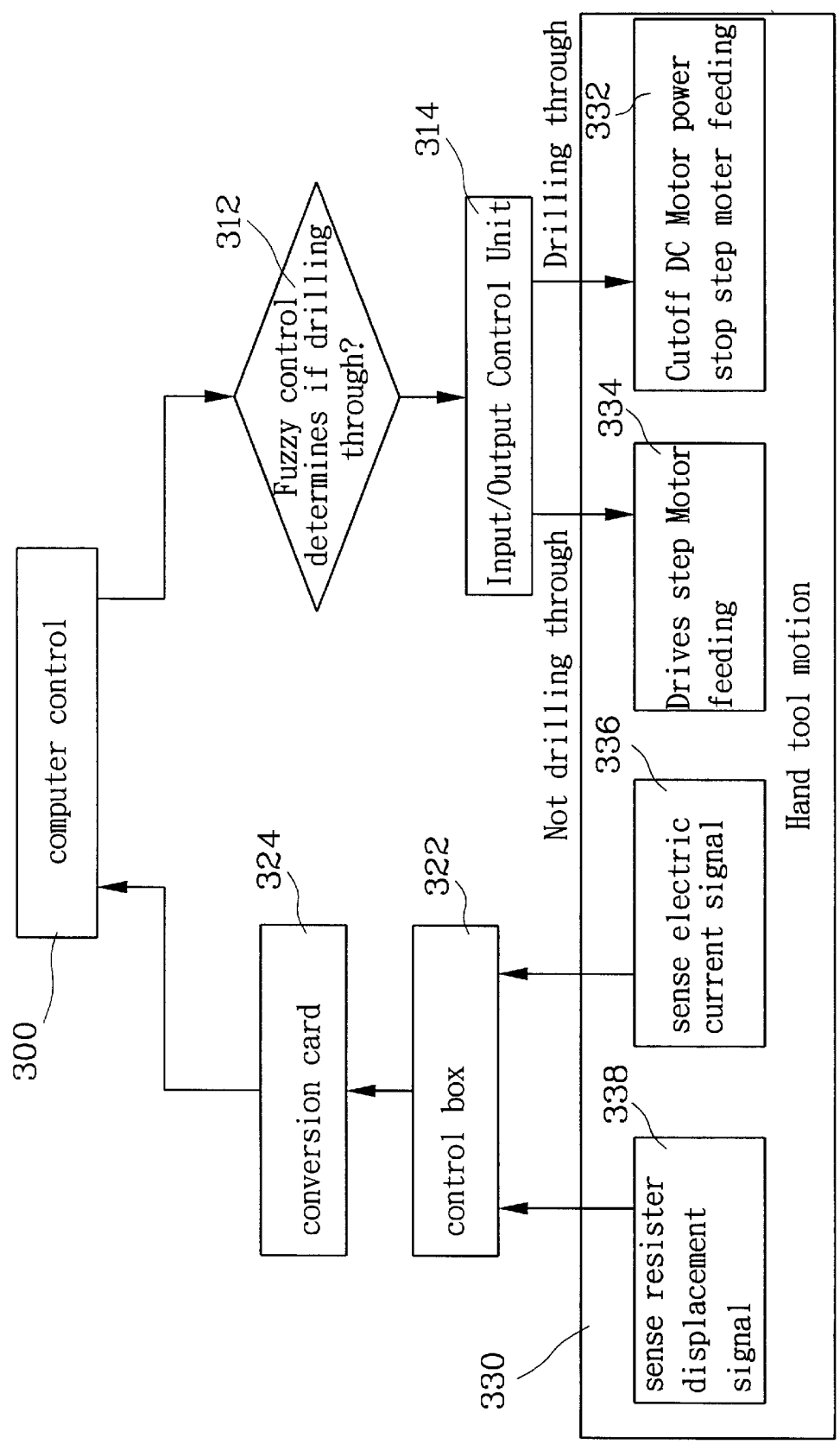
FIG. 3 is an operation flowchart of this invention.

FIG. 3 illustrates operation flow of this invention. Computer (300) has fuzzy logic software resided inside to determine if drilling through of the skeleton is reached (312) and through an input/output control unit (314) to instruct a hand tool (330) to proceed drilling or stop-drilling operation. Hand tool (330) feedbacks drilling status and conditions to a control box (322) which sends control signals to a conversion card (324) and transmits to the computer (300) to complete a closed loop control and operation. The following is the detailed processing procedure:

a. computer (300) initiates execution of fuzzy logic software control operation, b. fuzzy logic control detects and receives hand tool operation data and determines if a through opening is being drilled in the skeleton (312), and transmits signals to the input/output control unit (314), c. the input/output control unit (314) generates signals according to detecting results from the step b, d-1. cutoff power supply to the step motor (332) to stop drilling when detecting result shows a through opening in the bone is obtained d-2. drives the step motor to continue drilling operation (334) when detecting result shows a through opening is not yet obtained.

d-3. hand tool has built in instruments to detect working condition and status, and generates sensed electric current signals (336) to the control box (322), d-4. motion and displacement of the drill gimlet induces the generation of sense resistor displacement signal (338) which is also fed to the control box (322), e. the control box (322) receives signals from the hand tool (330), performs process required and feeds signals to the conversion card (324), f. the A/D conversion card (324) converts signals received from the control box (322) and feeds to the computer (300) for control operation desired.

By means of aforesaid procedure, skeleton or skeleton drilling operation may be performed safely and easier.

The fuzzy logic software in the computer 300 uses the conversion card to do analog/digital signal conversion to provide signals for processing and drilling operation. When a through opening is being detected in skeleton drilling, power supply to the hand tool is cutoff and the DC motor stops the drilling operation. The step motor is also being signaled to stop moving the drilling gimlet to avoid hurting brain which is under surgery operation. The hand tool includes drilling means in which a resistor ruler is located for measuring drilling gimlet displacement. The displacement includes signal transmitting to the control box.

Figure 4:
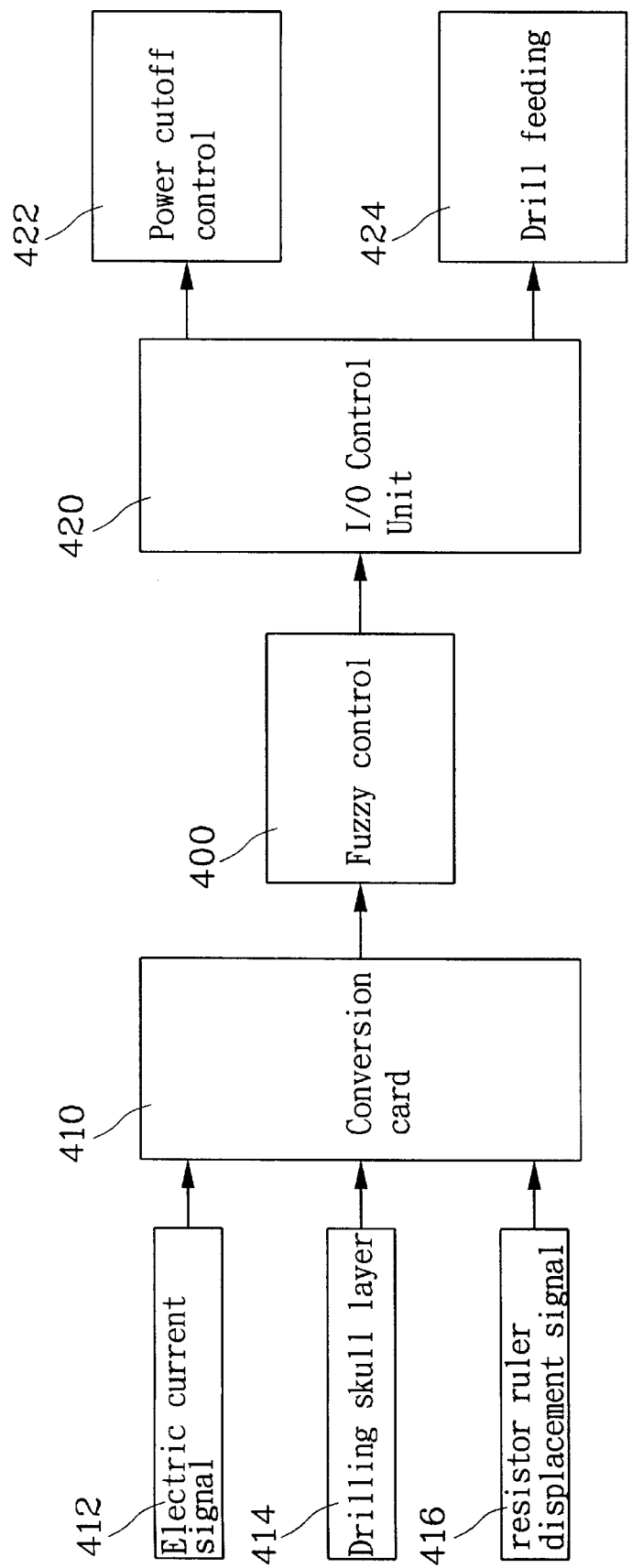
FIG. 4 is a flowchart of fuzzy logic operation used in this invention.

FIG. 4 illustrates fizzy logic principle used in this invention. A fuzzy control software 400 is resided in the computer lo monitor and control processes, including the followings:

a. in the hand tool, electric current signal 412, drilling skeleton layer 414 and resistor ruler displacement signal 416 are detected and sent to the conversion card 410 which has a sensing unit to detect hand tool operation status and generate the signals;

b. the conversion card 410 performs analog/digital signal conversion and sends out digital signals to the fuzzy control 400 for calculation and processing, c. the fuzzy control 400 generates control signal for skeleton drilling to the input/output control unit 420;

d. input/output control unit 420 generates instructions for either cutoff power supply 422 or continuing drill feeding 424 of the drilling device.

By means of the hardware structure and fuzzy logic software control, the hand tool may be used by surgeons to perform precise and delicate skeleton drilling at exact location so that brain surgical operation may be performed safely and smoothly with less guess work.

It may thus be sent that the objects of the present invention set forth herein, as well as those made apparent from the foregoing description, are efficiently attained. While the preferred embodiment of the invention have been set forth for purpose of disclosure, modifications of the disclosed embodiment of the invention as well as other embodiments thereof may occur to skilled in the art. Accordingly, the appended claims are intended to cover all embodiments which do not depart from the spirit and scope of the invention.

What is claimed is:

1. An automatic bone drilling apparatus for surgery operation, comprising:

a computer including an input output control card and a conversion card for analog digital signal conversion;

a control box wired to the computer and actuated by an electric voltage including a power switch for activating the control box, an indicator light for alerting skeleton drill through condition, a plurality of connector slots to engage with connection interface cards for signal transmission, and a hand tool output for supplying power and control signals; and a hand tool drilling device received the power and control signals from the control box to perform or stop drilling operation.

2. The automatic bone drilling apparatus of claim 1, wherein the computer uses a fuzzy logic control for receiving and processing signals and generating control signals to the control box for controlling the hand tool operation.

3. The automatic bone drilling apparatus of claim 2, wherein the fuzzy logic control includes the following steps:

a. the hand tool drilling device detecting and sending electric current signals, drilling skeleton layer and resistor ruler displacement signal to the conversion card;

b. the conversion card performing analog-digital signal conversion and output digital signals feeding to the computer fuzzy logic control;

c. the computer generating control signals;

d. an input output control unit receiving the control signals from the computer and issuing working instructions to the hand tool for performing drilling operation.

4. The automatic bone drilling apparatus of claim 3, wherein the control box further includes a sensor means for sensing the hand tool operation including current signal of a DC motor, resistor ruler displacement signal and signals of drilling skeleton layer.

5. The automatic bone drilling apparatus of claim 3, wherein the working instructions include power cutoff control signals and drill feeding signals for controlling operation of the hand tool drilling device.

6. The automatic bone drilling apparatus of claim 1, wherein the control box communicates with a manual-automatic mode switch box which has a switch for selecting an operation mode desired.

7. The automatic bone drilling apparatus of claim 1, wherein the control box communicates with an oscilloscope which has a display screen for indicating electric current in the hand tool drilling device.

8. The automatic bone drilling apparatus of claim 1, wherein the hand tool drilling device is a bone drilling means which includes a drill gimlet for drilling the skeleton, a DC motor actuated by the control signals for driving the drill gimlet, a slide block for holding and moving the DC motor and drill gimlet, and a rotation handle bar for moving the drill gimlet manually through a step motor.

9. The automatic bone drilling apparatus of claim 8, wherein the drilling device further includes a strut for supporting the drilling device and a pillar which has a holding bar for the drilling device to be held whereby.

10. The automatic bone drilling apparatus of claim 9, wherein the step motor may be braked through energized stator coil after receiving a control signal through the drilling device to prevent the drill gimlet from excessive drilling.

11. The automatic bone drilling apparatus of claim 1, wherein the hand tool is a drilling device which has a drilling gimlet producing a linear displacement during drill operation, the linear displacement is measured by a resistor ruler located in the control box for controlling drill operation.

12. An automatic bone drilling apparatus for surgery operation includes a computer run by a fuzzy logic software to control a hand tool to drill an opening in skeleton, an input output control unit for signal transmission, a control box and a conversion card for controlling the hand tool which has a drill gimlet driven by a DC motor, the hand tool being operated by the following steps:

a. the computer initiating a fuzzy logic control process, b. the computer fuzzy logic software receiving data and detecting if a through opening has been drilled in the bone by the hand tool;

c. the input output control device issuing instructions based on outcome of the step b;

d-1. cutting off power supply to stop DC motor for stopping drill feeding when through opening detection is positive;

d-2. continuing driving the DC motor for drill feeding operation when through opening detection is negative;

d-3. sensing electric current signal by instruments located in the hand tool and transmitting the electric current signals to the control box;

d-4. sensing resistor ruler displacement signal by the instruments and transmitting the displacement signal to the control box;

e. the control box receiving signals from the hand tool;

f. the conversion card receiving signals from the control box and converting and transmitting signals to the computer for controlling bone drilling operation.

13. The automatic bone drilling apparatus of claim 12, wherein the fuzzy logic software performs desired process after receiving data signals from the conversion card.

14. The automatic bone drilling apparatus of claim 12, wherein power supply to the hand tool is cutoff to stop the DC motor and prevent the drill gimlet from drill feeding by the motor or human labor after a through opening has been detected.

15. The automatic bone drilling apparatus of claim 12, wherein the control box includes a power switch for actuating the control box, an indicator light for alerting skeleton drill through condition, a plurality of connector slots to engage with connection interface cards for signal transmission, and a hand tool output for transmitting signals to the hand tool, the control box wires to a manual-automatic mode switch box for selecting hand tool operation mode and an oscillator.

16. The automatic bone drilling apparatus of claim 12, wherein the conversion card performs analog to digital signal conversion.

* * * * *